United States Patent
Vila Pahi et al.

(10) Patent No.: US 7,141,556 B2
(45) Date of Patent: Nov. 28, 2006

(54) PROCESS FOR THE PREPARATION OF GLUCOSAMINE SALTS

(75) Inventors: Francisco Javier Vila Pahi, Barcelona (ES); Ricard Mis Vizcaino, Sant Cugat del Valles (ES); Ramon Ruhi Roura, Barcelona (ES); Ana Maria Torrent Gibert, Massanes (ES); Vicente Montiel Leguey, Santa Pola (ES); Vicente Garcia Garcia, Alicante (ES); Eduardo Exposito Rodriguez, Alicante (ES); Antonio Aldaz Riera, El Campello (ES); Carlos Raul Alaez Verson, Blanes (ES)

(73) Assignee: Bioiberica, S.A., Barcelona (ES)

( * ) Notice: Subject to any disclaimer, the term of this patent is extended or adjusted under 35 U.S.C. 154(b) by 104 days.

(21) Appl. No.: 10/498,055

(22) PCT Filed: Dec. 13, 2002

(86) PCT No.: PCT/EP02/14225

§ 371 (c)(1),
(2), (4) Date: Jun. 9, 2004

(87) PCT Pub. No.: WO03/053448

PCT Pub. Date: Jul. 3, 2003

(65) Prior Publication Data

US 2005/0014720 A1   Jan. 20, 2005

(30) Foreign Application Priority Data

Dec. 21, 2001   (ES) .............................. 200102856

(51) Int. Cl.
*A61K 31/7008* (2006.01)
*C07H 5/06* (2006.01)
*C25B 3/00* (2006.01)

(52) U.S. Cl. .................. 514/62; 536/55.2; 205/421
(58) Field of Classification Search .................. 514/62; 536/55.2; 205/421
See application file for complete search history.

(56) References Cited

U.S. PATENT DOCUMENTS 3,683,076 A      8/1972   Luigi et al.
5,902,801 A *    5/1999   Schleck et al. ............... 514/62

FOREIGN PATENT DOCUMENTS

| CH | 525 861 | 7/1972 |
| GB | 1 056 331 | 1/1967 |
| WO | WO 01/82938 | * 11/2001 |
| WO | WO 02 066667 | 8/2002 |

* cited by examiner

*Primary Examiner*—Shaojia A. Jiang
*Assistant Examiner*—Ganapathy Krishnan
(74) *Attorney, Agent, or Firm*—Sughrue Mion, PLLC

(57) ABSTRACT

This invention relates to a process for the preparation of glucosamine sulfate, glucosamine hydroiodide, glucosamine pyruvate, glucosamine phosphate or their mixtures with glucosamine hydrochloride, by electrodialysis. Starting from glucosamine hydrochloride, the exchange of the Cl$^-$ for an anion selected from the group consisting of SO$_4^{-2}$, I$^-$, CH$_3$COCOO$^-$ and PO$_4^{-3}$ takes place during the process. The electrodialyser comprises a cathode, anode, and means of separation composed of anion exchange membranes, cation exchange membranes, bipolar membranes or by other suitable means of separation. This invention also relates to a glycosamine sulphate containing chlorides obtainable by the process, and its therapeutic use.

21 Claims, 2 Drawing Sheets

Figure 1:
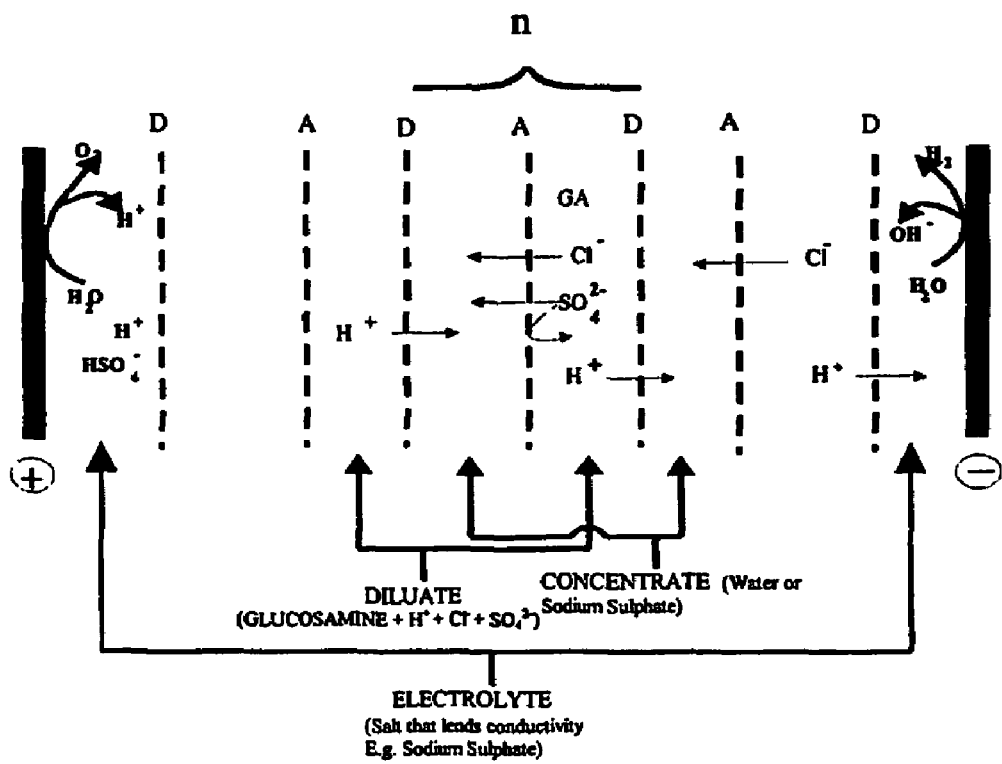

A= Monoselective or non-monoselective anion exchange membrane

D= Cation exchange membrane or bipolar membrane

GA= Glucosamine

A1 = Monoselective or non-monoselective anion exchange membrane
A2 = Anion exchange membrane
C = Cation exchange membrane
GA = Glucosamine

PROCESS FOR THE PREPARATION OF GLUCOSAMINE SALTS

CROSS-REFERENCE TO RELATED APPLICATION

This application is a 371 of PCT/EPO2/14225, filed Dec. 13, 2002; the disclosure of which is incorporated herein by reference.

DESCRIPTION

Technical Sector of the Invention

This invention relates to a process for the preparation of glucosamine sulphate, glucosamine hydroiodide, glucosamine pyruvate, glucosamine phosphate or their mixtures with glucosamine hydrochloride. This invention also refers to a glucosamine sulphate containing chlorides obtainable by the process, and its therapeutical use.

State of the Art in Relation to the Invention

Electrodialysis is a technique that uses ion exchange membranes and permits to separate dissolved ionic substances when a difference of potential is applied. It is a process widely used to obtain drinking water, generally from salt water, in the treatment of industrial effluents and, in addition, in the food and pharmaceutical industries, where it is being fully developed, it is used, for instance, to separate and purify solutions.

Glucosamine is a well-known substance, used in the treatment of osteoarthritis and arthritis in general, in both acute and chronic forms, as well as in the treatment of pathological conditions affecting the osteo-articular tissue.

The fact that the glucosamine base is an unstable substance has lead to its commercialisation as different salts, which maintain the same pharmacological properties (L. Rovati, U.S. Pat. No. 3,683,076, H. Müller-Faβbender et al., *Osteoarthritis Cart.*, 2 (1994)).

Various processes to obtain glucosamine salts are known. Some of them consist of previously obtaining the glucosamine base from glucosamine hydrochloride, later adding the corresponding acid, depending on the salt desired. In general, to obtain the glucosamine base, glucosamine hydrochloride is treated with triethylamine (L. Rovati, CH 525, 861), or with sodium methoxide (L. Rovati, U.S. Pat. No. 3,683,076) or by means of anion exchange resins. These processes have the disadvantage of having to previously go through a product as unstable as glucosamine base, and of using, in some cases, toxic substances such as triethylamine. The salts can also be obtained directly, starting from glucosamine hydrochloride and using an anion exchange resin previously treated with the acid that contains the anion of the salt desired, or a metal salt of one of said acids (GB 1,056,331). As this process uses resins it has the disadvantage of giving a low production yield.

In accordance with this, it is necessary to find an alternative method for the preparation of said glucosamine salts, avoiding the above-mentioned disadvantages of the traditional methods.

Until now, no process has been disclosed for the preparation of the glucosamine salts of this invention using an electrochemical technology called electrodialysis.

DISCLOSURE OF THE INVENTION

This invention relates to a process for the preparation of glucosamine sulphate, glucosamine hydroiodide, glucosamine pyruvate, glucosamine phosphate or their mixtures with glucosamine hydrochloride by means of electrodialysis.

In a preferred embodiment, starting from glucosamine hydrochloride, the exchange of the Cl⁻ anion for an anion, selected from the group consisting of $SO_4^{2-}$, $I^-$, $CH_3COCOO^-$ and $PO_4^{3-}$, takes place during the process of electrodialysis. $SO_4^{2-}$ is the preferred anion amongst these, obtaining glucosamine sulphate. Preferably the preparation process of glucosamine sulphate, glucosamine hydroiodide, glucosamine pyruvate, glucosamine phosphate or their mixtures with glucosamine hydrochloride by electrodialysis, comprises the following steps:

(a) preparation of an aqueous solution composed of glucosamine hydrochloride; preparation of an aqueous solution of a salt or of the acid that contains the anion to be exchanged for the chloride anion, in order to feed the diluate; preparation of an aqueous solution of a salt that lends conductivity, in order to feed the electrolyte and preparation of a container with water or an aqueous solution of a salt that contains the anion to be exchanged for the chloride anion, in order to feed the concentrate; a soluble hydroxide of an alkaline or alkaline earth metal is added to the concentrate throughout the process in order to keep its pH higher than 2;

(b) feeding of the diluate, electrolyte and concentrate compartments;

(c) application of an electric field so that the current intensity is constant or variable throughout the process or operating at a controlled difference of potential;

(d) verification of the chloride content in the diluate;

(e) turning off the power once the desired amount of chlorides is obtained;

(f) recovery of the solution that comes from the diluate; and (g) obtaining the solid product by atomisation, lyophilisation, or another alternative procedure;

or otherwise the preparation process of glucosamine sulphate, glucosamine hydroiodide, glucosamine pyruvate, glucosamine phosphate or their mixtures with glucosamine hydrochloride by electrodialysis, comprises preferably the following steps:

(a) preparation of an aqueous solution composed of glucosamine hydrochloride, to feed the diluate 1; preparation of an aqueous solution of the salt that contains the anion to be exchanged for the chloride anion, in order to feed the diluate 2; preparation of an aqueous solution of a salt that lends conductivity, in order to feed the electrolyte, and preparation of a container with water or an aqueous solution of a salt that contains the anion to be exchanged for the chloride anion, in order to feed the concentrate;

(b) feeding of the diluate 1, diluate 2, electrolyte and concentrate compartments;

(c) application of an electric field so that the current intensity is constant or variable throughout the process or operating at a controlled difference of potential;

(d) verification of the chloride content in the diluate;

(e) turning off the power once the desired amount of chlorides is obtained;

(f) recovery of the solution that comes from the diluate; and (g) obtaining the solid product by atomisation, lyophilisation, or another alternative procedure.

The electrodialysis is preferably carried out in an electrodialyser or stack of electrodialysis, which is comprised of a cathode, an anode and means of separation, which are preferably composed of anion exchange membranes, cation exchange membranes, bipolar membranes or by means of other suitable means of separation.

An electrode made of graphite, coal or its derivates, lead, tin, zinc, copper, platinized titanium, all kinds of steel or alloys of iron, aluminium or its alloys with gallium, indium or thallium, a gas-diffusion cathode, or a DSE cathode are preferably used for the cathode.

A stable electrode selected from Ti—Pt, Ti—Pb, DSA oxygen, DSA chloride, $PbO_2$, vitreous carbons, graphite, DSE, and a gas-diffusion anode can be used for the anode.

The cathode and the anode should not restrict the invention.

The anion and cation exchange membranes can be chosen from those commercialised, such as, e.g. Nafion, Neosepta, Aciplex, Sybron, Ionics, Aqualytic, or any other one commercialised.

Any bipolar membrane existing on the market can be used, e.g. the Tokuyama Soda BP1.

The electrodialysis process is preferably carried out at a temperature from 0 to 90° C.

The final chloride content is preferably from 0.5 to 16% solid product.

Likewise, the final chloride content is preferably lower than 0.5% solid product.

The solution that comes from the diluate of the electrodialyser or the solid product obtained by atomisation, lyophilisation or by other alternative means, can be subjected to any process for the purpose of obtaining a product suitable for use in oral, injectable or topical pharmaceutical preparations.

In another preferred embodiment, the solution that comes from the diluate of the electrodialyser is mixed with a sodium or potassium salt or with an aqueous solution of a sodium or potassium salt, and the product is subsequently obtained in a solid form by a drying process, previous precipitation with organic solvents that are miscible with water, by atomisation, by lyophilisation, or by another alternative method.

Figure 2:
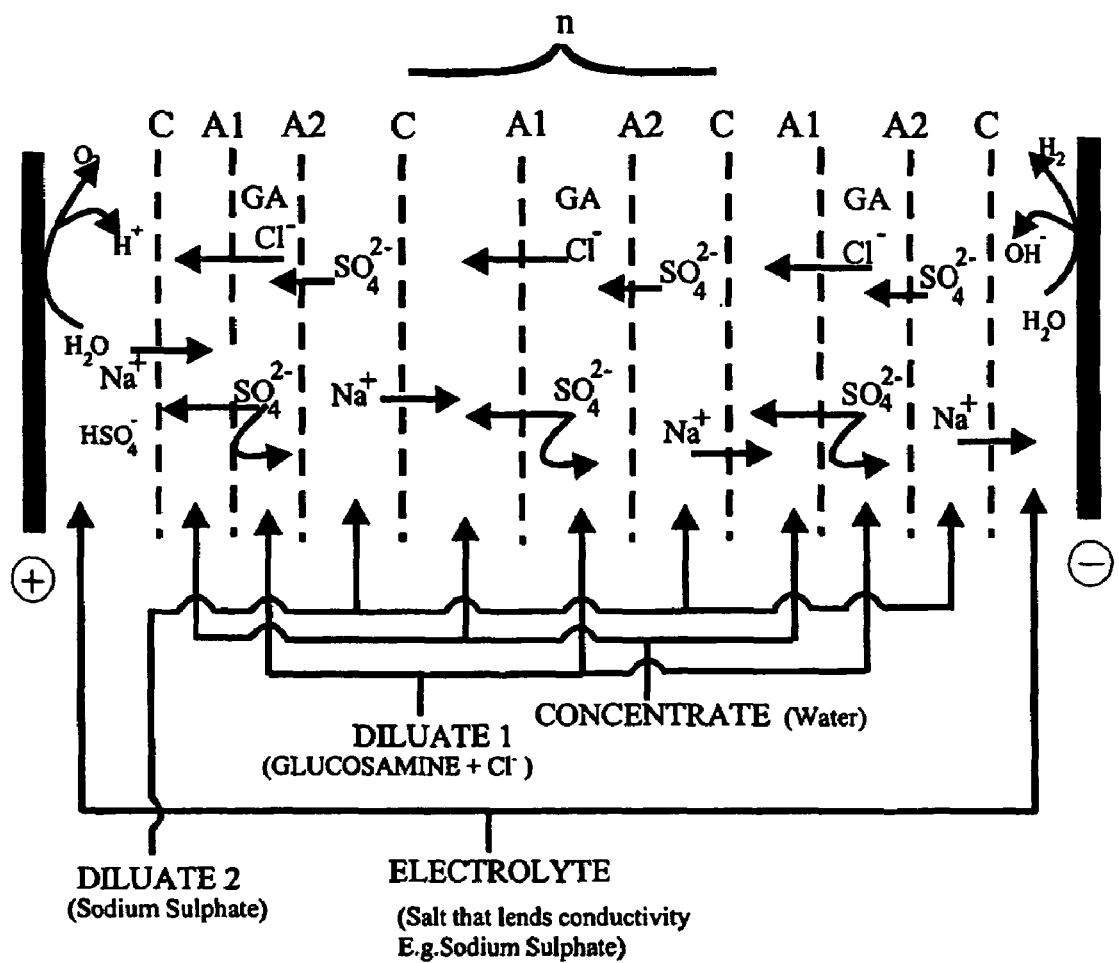

There are several types of stacks of electrodialysis, which can be used for the preparation of the salts of the present invention, e.g. those of FIGS. 1 and 2.

In FIG. 1, an electrodialyser to be used in the invention according to claim 4 is viewed, and FIG. 2 is a diagram of another electrodialyser to be used in the invention according to claim 5. In FIGS. 1 and 2, the process of obtaining the glucosamine sulphate is viewed.

In a type of electrodialyser such as that of FIG. 1, to which the steps of the process of claim 4 will be applied, an alternated combination of anion exchange membranes (monoselective or non-monoselective membranes) and cation exchange membranes, or an alternated combination of anion exchange membranes (monoselective or non-monoselective membranes) and bipolar membranes is used. In this case it is a three compartment electrodialysis system: diluate, concentrate and electrolyte. The diluate is fed with a solution prepared from glucosamine hydrochloride and the acid or salt that contains the anion to be exchanged for the chloride, depending on the case. In order to maintain the pH higher than 2, a soluble hydroxide of an alkaline or alkaline earth metal is added to the concentrate. When an electric field is established, the $Cl^-$ anions will leave the diluate solution through the anion exchange membrane. In this manner, if desired, a point can be reached at which practically all the chlorides have left the diluate, i.e. the $Cl^-$ anions will be exchanged for the $SO_4^{2-}$, $I^-$, $CH_3COCOO^-$ or $PO_4^{3-}$ anions.

In a type of electrodialyser such as that of FIG. 2, to which the steps of the process of claim 5 will be applied, an alternated combination of cation exchange membranes, monoselective or non-monoselective anion exchange membranes and anion exchange membranes is used. The diluate 1 is fed with a glucosamine hydrochloride solution, which will lose the $Cl^-$ anion through the monoselective or non-monoselective anion exchange membrane and will receive the $SO_4^{2-}$, $I^-$, $CH_3COCOO^-$ or $PO_4^{3-}$ anions, depending on the case, through the anion exchange membrane. Thus, the $Cl^-$ anions will be exchanged for the $SO_4^{2-}$, $I^-$, $CH_3COCOO^-$ or $PO_4^{3-}$ in the diluate.

In both cases, the electrodialysis is maintained until the chloride content reaches the desired limit. The Mohr method is used to determine the chlorides (I. M. Kolthoff et al. "Análisis Quimico Cuantitativo", 4th edition, Ed. Nigar, Buenos Aires, 1972).

The present invention also refers to glucosamine sulphate with a chloride content from 0.5 to 16% solid product obtainable by the process of the present invention.

Another aspect of the present invention is a pharmaceutical or veterinary composition comprising glucosamine sulphate with a chloride content from 0.5 to 16% solid product, and a pharmaceutically acceptable carrier.

Another aspect of the present invention is the use of glucosamine sulphate with a chloride content from 0.5 to 16% solid product, for the manufacture of a medicament for the treatment or prevention of arthritis.

Preferably the arthritis is osteoarthritis.

One advantage of this process, compared to those known in the art, lies in the fact that a product as unstable as the glucosamine base is not isolated at any time.

Another important advantage is that a substance such as triethylamine, that is toxic even in small quantities, is not used.

Another advantage compared to the processes that use ion exchange resins, is that it is a more profitable process, with a lower cost.

DETAILED DESCRIPTION OF THE PREFERRED EMBODIMENTS

The following examples are not restrictive and illustrate the preparation process of the salts of this invention.

EXAMPLE 1

Preparation of Glucosamine Sulphate According to the Process of FIG. 2 (Current Intensity 10 A)

A stack of electrodialysis was set up (according to FIG. 2) with two electrodes and 10 unit cells, the anode being composed of Ti—Pt and the cathode of stainless steel. The unit cell is comprised of two anion exchange membranes that allow all anions to pass through (Tokuyama Neosepta AMX) and a cation exchange membrane that allows all cations to pass through (Tokuyama Neosepta CMX).

Next, the glucosamine hydrochloride and sodium sulphate solutions were prepared.

10 L of a 17% (w/v) glucosamine hydrochloride solution were prepared and loaded in a PVC tank used to feed the diluate 1.

The electrolyte solution, consisting of 2 L of a 1.4% (w/w) sodium sulphate solution was prepared. Once prepared, it was loaded in a tank used to feed the electrolyte.

The diluate 2 solution, consisting of 20 L of 10% (w/v) sodium sulphate, was prepared. Once prepared, it was loaded in the tank used to feed the diluate 2.

20 L of decalcified water were loaded in the tank used to feed the concentrate.

The solutions contained in the tank were driven by means of a pump and were made to pass through a 10–20 micron filter before feeding the compartments. The flow of the pumps of the concentrate and of both diluates was set to 300 L/h and those of the electrolyte to 150 L/h.

In order to promote the migration of the ions, an electric field was applied, making a current pass between the anode and the cathode. The intensity was maintained constant at 10 A, setting a difference of potential of 40 V between both electrodes. The current was transported through the solution by means of both the anions and the cations, according to their corresponding transport numbers.

The solutions were maintained in recirculation until reaching a chloride concentration of the diluate 1 solution (solution where the glucosamine hydrochloride had been added) lower than 0.085%.

The desired chloride levels were reached approximately 9 hours after the start of the reaction.

During the process, samples were taken and the chloride concentration present both in the diluate and in the concentrate, was determined.

After 590 minutes, and because the amount of chlorides of the diluate solution had reached the desired level, the current was turned off.

The diluate solution was subjected to a lyophilisation process in order to obtain the solid product (glucosamine sulphate), a white-coloured solid (yield higher than 95%), with a melting point of 128° C. with decomposition being obtained.

Assay: 96.6%

Chloride content: 0.48% on dry base

IR (KBr) cm$^{-1}$: 3600–3100, 3090–3030, 2935, 1610, 1530, 1420, 1420–1070, 1040. NMR of $^{13}$C (D$_2$O) δ ppm: 95.65 (C1β), 92.08 (C1α), 79.08 (C5β),74.89 (C3 β), 74.55 (C5α), 72.53 and 72.66 (C4α, C4β, C3α), 63.44 and 63.30 (C6α, C6β),59.72 (C2β) and 57.3 (C2α).

EXAMPLE 2

Preparation of Glucosamine Sulphate According to the Process of FIG. 2 (Current Intensity 14 A)

The process in Example 1 was followed, but in this case 10 L of 21% glucosamine hydrochloride, 2 L of a 1.4% (w/w) sodium sulphate solution as electrolyte solution and a current intensity of 14 A were used, setting a difference of potential between both electrodes of 50 V.

The diluate solution was subjected to a lyophilisation process in order to obtain the solid product (glucosamine sulphate), a white-Coloured solid (yield higher than 95%), with a melting point of 128° C. with decomposition being obtained.

The product obtained, as regards analytical and spectroscopic results, is equivalent to the product obtained in Example 1.

EXAMPLE 3

Glucosamine Sulphate Preparation According to the Process of FIG. 1 (Monoselective Anion Exchange Membranes and Cation Exchange Membranes)

A Eurodia EUR 6-80 stack of electrodialysis was used (according to FIG. 1). The stack consisted of 80 unit cells, with a total active surface area of 4.4 m².

The cation exchange membrane used was the Tokuyama Soda CMX-SB and the anion exchange membrane was the Tokuyama Soda ACS. Eurodia DSE was used as the anode and cathode.

The resulting system has three compartments: diluate, concentrate and electrolyte.

Next, the solutions to feed the diluate and electrolyte were prepared.

A solution with 9.2 Kg of glucosamine hydrochloride and 38.4 Kg of water, and sulphuric acid until reaching 4.9% (w/w), was used for the diluate. 500 L of decalcified water were initially used for the concentrate. A 1.4% (w/w) solution of sodium sulphate was used for the electrolyte.

The experiment was carried out at room temperature with the following program of difference of potential against time:

| From 0 to 0.8 h | 100 V |
|---|---|
| From 0.8 h to the end | 75 V |

Sodium hydroxide was added to the concentrate so that its pH was higher than 2.

The solutions were maintained in recirculation until the desired chloride concentration was obtained in the diluate. The detection of the final point was carried out by means of a chloride analysis according to the Mohr method.

The experiment lasted 4.3 hours, obtaining a 0.004% (w/w) chloride concentration in the diluate.

The monitoring of the reaction can be observed in Table 1.

The glucosamine sulphate was obtained by lyophilisation, white-coloured solid (yield higher than 95%) being obtained.

Assay: 97.7%

Chloride content: 0.02% on dry base

TABLE 1

| Time (h) | Voltage (V) | % Cl$^-$ (diluate) | % Cl$^-$ (dry base) diluate | % SO$_4^{2-}$ (diluate) | pH (diluate) |
|---|---|---|---|---|---|
| 0 | 96 | 2.670 | | 4.79 | 0.5 |
| 0.3 | 98 | 1.540 | 8.9 | 4.55 | 0.8 |
| 1.0 | 74 | 0.860 | 5.0 | 4.15 | 1.5 |
| 1.6 | 74 | 0.190 | 1.1 | 3.77 | 2.0 |
| 2.2 | 74 | 0.082 | 0.49 | 3.69 | 2.5 |
| 2.8 | 74 | 0.030 | 0.18 | 3.67 | 2.6 |
| 4.3 | 74 | 0.004 | 0.02 | 3.46 | 3.2 |

EXAMPLE 4

Preparation of Glucosamine Sulphate According to the Process of FIG. 1 (Monoselective Anion Exchange Membranes and Bipolar Membranes)

A Eurodia TS-2-10-P stack of electrodialysis was used. The stack consisted of 10 unit cells, with a total active surface area of 0.2 m².

The bipolar membrane used was the Tokuyama Soda BP1 and the anion exchange membrane used was the Tokuyama Soda ACS. Stainless steel was used as a cathode and Ti/Pt as the anode.

Next, the solutions to feed the diluate concentrate and electrolyte were prepared.

An aqueous solution of 18% (w/w) glucosamine hydrochloride and 7.3% (w/w) sulphuric acid was used for the diluate. A 0.44% (w/w) sodium sulphate solution was used for the concentrate. A 1.4% (w/w) sodium sulphate solution was used for the electrolyte.

The experiment was carried out at a temperature below 40° C. and at a controlled Intensity, applying the following program of intensity against time:

| From 0 to 0.32 h | 3.3 A |
| From 0.32 to 2.4 h | 4.0 A |
| From 2.4 to 2.7 h | 3.0 A |
| From 2.7 to 3.6 h | 2.3 A |
| From 3.6 to 4.6 h | 2.0 A |
| From 4.6 to 6.0 h | 1.4 A |
| From 6.0 to 7.5 h | 1.0 A |
| From 7.5 to 13.2 h | 0.8 A |

When the specific conductivity of the concentrate reached 20 mS/cm, half of the concentrate was unloaded and replaced by the same quantity of water.

The experiment lasted 13.2 hours, obtaining a 0.029% (w/w) chloride concentration in the diluate. The monitoring of the reaction can be observed in Table 2.

The glucosamine sulphate was obtained by lyophilisation, a white-coloured solid (yield higher than 95%) being obtained.

Assay: 97.6%

Chloride content: 0.16% on dry base

TABLE 2

| Time (h) | Voltage (V) | % Cl$^-$ (diluate) | % Cl$^-$ (dry base) (diluate) | % SO$_4^{2-}$ (diluate) | pH (diluate) |
| --- | --- | --- | --- | --- | --- |
| 0 | 16.0 | 2.900 | | 7.62 | 0.0 |
| 1.2 | 19.7 | 2.140 | 12 | 6.61 | 0.1 |
| 2.1 | 19.0 | 1.650 | 8.9 | 6.34 | 0.3 |
| 3.3 | 14.6 | 1.190 | 6.3 | 5.81 | 0.6 |
| 4.6 | 12.3 | 0.740 | 4.0 | 5.12 | 0.9 |
| 7.5 | 11.4 | 0.290 | 1.5 | 4.24 | 1.5 |
| 13.2 | 11.3 | 0.029 | 0.16 | 4.01 | 2.8 |

The invention claimed is:

1. A process for preparing glucosamine sulphate, glucosamine hydroiodide, glucosamine pyruvate or glucosamine phosphate or mixtures thereof with glucosamine hydrochloride, said process comprising the step of subjecting glucosamine hydrochloride to electrodialysis.

2. The process according to claim 1, wherein during said electrodialysis, Cl$^-$ anion in glucosamine hydrochloride is exchanged for an anion selected from the group consisting of SO$_4^{-2}$, I$^-$, CH$_3$COCOO$^-$ and PO$_4^{-3}$.

3. The process according to claim 2, wherein during said electrodialysis, Cl$^-$ anion in glucosamine hydrochloride is exchanged for SO$_4^{-2}$ anion to thereby obtain glucosamine sulphate.

4. The process according to any one of claims 1 to 3 wherein said process comprises the following steps:
(a) providing a stack of electrodialysis compartments, and feeding (i) a diluate compartment, (ii) an electrolyte compartment and (iii) a concentrate compartment thereof,
wherein said diluate compartment, after said feeding, comprises an aqueous solution of glucosamine hydrochloride and an aqueous solution of a salt or of an acid that contains an anion to be exchanged for Cl$^-$ anion,
wherein said electrolyte compartment, after said feeding, comprises an aqueous solution of a salt that lends conductivity,
wherein said concentrate compartment, after said feeding, comprises water or an aqueous solution of a salt that contains the anion to be exchanged for the Cl$^-$ anion;
(b) applying an electrical field across said stack of electrodialysis compartments at a constant or variable current intensity or at a controlled potential difference;
(c) assaying the Cl$^-$ content in the diluate compartment, and discontinuing electrodialysis once a desired amount of chloride has been obtained;
(d) recovering the solution from the diluate compartment; and
(e) obtaining a solid product from said solution of step (d), wherein during said process a soluble hydroxide of an alkaline or alkaline earth metal is added to said concentrate compartment in order to maintain a pH greater than 2.

5. The process of claim 4, wherein said solid product in step (e) is obtained by atomizing or lyophilizing said solution.

6. The process of any one of claims 1 to 3, wherein said process comprises the following steps:
(a) providing a stack of electrodialysis compartments and feeding (i) a first diluate compartment, (ii) a second diluate compartment; (iii) an electrolyte compartment and (iv) a concentrate compartment thereof,
wherein said first diluate compartment, after said feeding, comprises an aqueous solution of glucosamine hydrochloride,
wherein said second diluate compartment, after said feeding, comprises an aqueous solution of a salt that contains an anion to be exchanged for CJJ anion,
wherein said electrolyte compartment comprises, after said feeding, an aqueous solution of a salt that lends conductivity,
wherein said concentrate compartment comprises, after said feeding, water or an aqueous solution of a salt that contains the anion to be exchanged for the Cl$^-$ anion
(b) applying an electrical field across said stack of electrodialysis compartments at a constant or variable current intensity or at a controlled potential difference;
(c) assaying the Cl$^-$ content in the first diluate compartment, and discontinuing electrodialysis once a desired amount of chloride has been obtained;
(d) recovering the solution from the first diluate compartment; and
(e) obtaining a solid product from said solution of step (d).

7. The process of claim 6, wherein said solid product in step (e) is obtained by atomizing or lyophilizing said solution.

8. The process according to claim 4, wherein electrodialysis is carried out in an electrodialyser which comprises a cathode, an anode and means of separation.

9. The process according to claim 6, wherein electrodialysis is carried out in an electrodialyser that comprises a cathode, an anode and means of separation.

10. The process according to claim 8, wherein the means of separation comprise an anion exchange membrane, cation exchange membrane, or bipolar membrane.

11. The process according to claim 9, wherein the means of separation comprise an anion exchange membrane, cation exchange membrane, or bipolar membrane.

12. The process according to claim 4, wherein electrodialysis is carried out at a temperature of from 0 to 90° C.

13. The process according to claim 4, wherein said solid product has a chloride content of from 0.5 to 16%.

14. The process according to claim 4, wherein said solid product has a chloride content of less than 0.5%.

15. The process according to claim 4, wherein the solution of step (d) or the solid product of step (e), is formulated into a product suitable for use in an oral, injectable or topical pharmaceutical preparation.

16. The process according to claim 4, wherein the solution of step (d) is mixed with a sodium or potassium salt, or with an aqueous solution of a sodium or potassium salt, and the product of step (e) is obtained in a solid form by drying said solution, by precipitating by adding an organic solvent that is miscible with water to said solution, by atomizing said solution, or by lyophilizing said solution.

17. The process according to claim 6, wherein electrodialysis is carried out at a temperature of from 0 to 90° C.

18. The process according to claim 6, wherein said solid product has a chloride content of from 0.5 to 16%.

19. The process according to claim 6, wherein said solid product has a chloride content of less than 0.5%.

20. The process according to claim 6, wherein the solution of step (d) or the solid product of step (e), is formulated into a product suitable for use in an oral, injectable or topical pharmaceutical preparation.

21. The process according to claim 6, wherein the solution of step (d) is mixed with a sodium or potassium salt, or with an aqueous solution of a sodium or potassium salt, and the product of step (e) is obtained in a solid form by drying said solution, by precipitating by adding an organic solvent that is miscible with water to said solution, by atomizing said solution, or by lyophilizing said solution.

* * * * *